Figure 1:
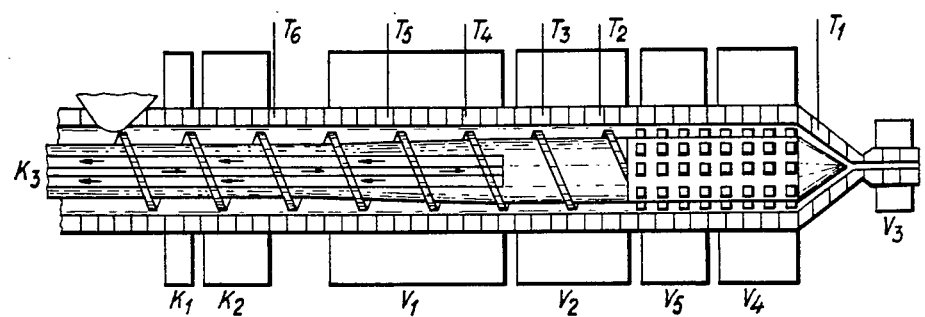

United States Patent [19]

Nieuwenhuis et al.

[11] Patent Number: 4,778,881

[45] Date of Patent: Oct. 18, 1988

[54] METHOD FOR THE PREPARATION OF ESTERS OF A NON-REDUCING SUGAR AND ONE OR MORE FATTY ACIDS

[75] Inventors: Hermanus J. W. Nieuwenhuis, Sprundel; Gerardus M. Vianen, Roosendaal, both of Netherlands

[73] Assignee: Cooperatieve Vereniging Suiker Unie U.A., Netherlands

[21] Appl. No.: 820,244

[22] Filed: Jan. 17, 1986

[30] Foreign Application Priority Data

Jan. 24, 1985 [NL] Netherlands ................... 8500191

[51] Int. Cl.$^4$ ............................................. C07H 13/06
[52] U.S. Cl. ..................................... 536/119; 536/115
[58] Field of Search ............................... 536/119, 115

[56] References Cited

U.S. PATENT DOCUMENTS

| | | | |
|---|---|---|---|
| 2,459,108 | 8/1946 | Loekema et al. | 536/120 |
| 2,976,131 | 3/1961 | Milne | 23/285 |
| 3,558,597 | 1/1971 | von Brachel et al. | 536/119 |

FOREIGN PATENT DOCUMENTS

| | | | |
|---|---|---|---|
| 2065634 | 7/1981 | United Kingdom | 536/115 |
| 2081266 | 2/1982 | United Kingdom | |

*Primary Examiner*—J. R. Brown
*Assistant Examiner*—Elli Peselev
*Attorney, Agent, or Firm*—Webb, Burden, Ziesenheim & Webb

[57] ABSTRACT

Method for the preparation of esters of a non-reducing sugar like sucrose and one or more fatty acids by transesterification of a non-reducing sugar with one or more fatty acid esters in at first a worm shaft reactor operating at elevated temperature and pressure and then in a second reactor operating at reduced pressure and elevated temperature. Such esters of a non-reducing sugar and fatty acids, in particular the monoesters and diesters are valuable solid surfactants, which are non-toxic, odorless, tasteless, non-irritating to the skin and hydrolyze in the human and animal tract to normal good products.

10 Claims, 3 Drawing Sheets

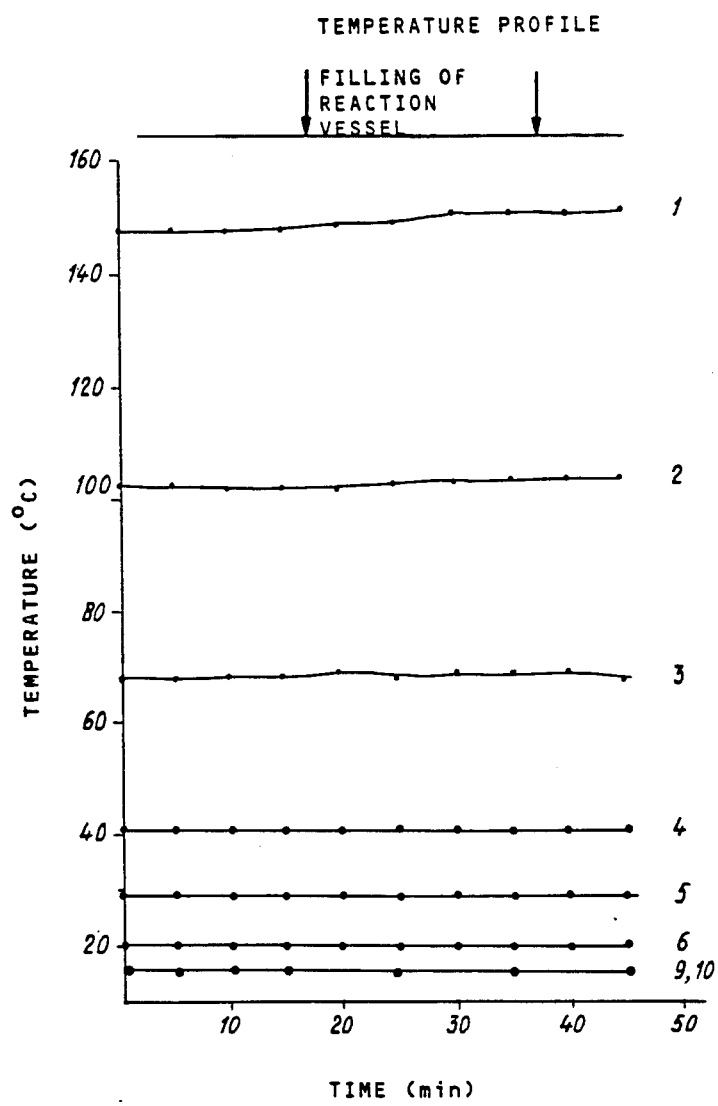

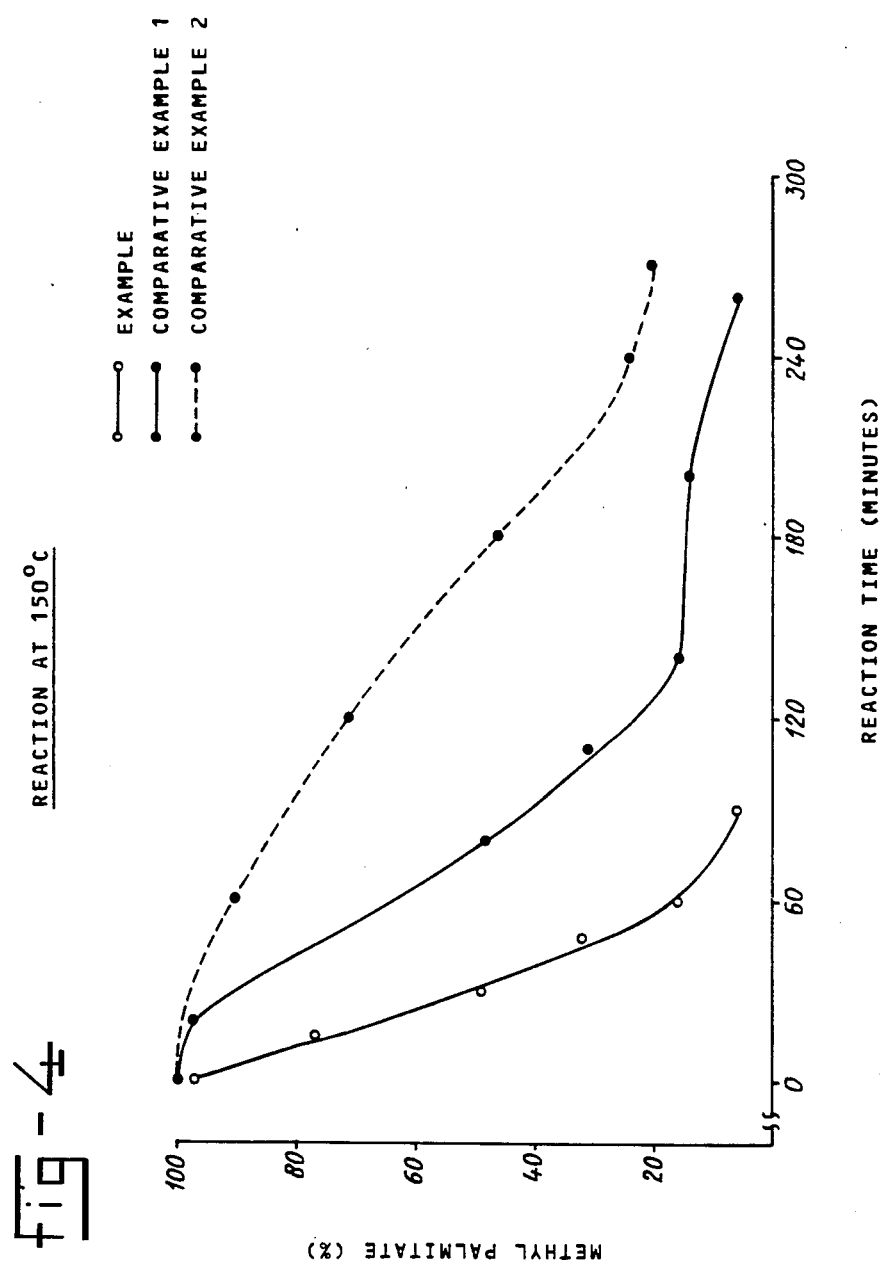

METHOD FOR THE PREPARATION OF ESTERS OF A NON-REDUCING SUGAR AND ONE OR MORE FATTY ACIDS

The invention relates to a method for the preparation of esters of a non-reducing sugar and one or more fatty acids by transesterification of a non-reducing sugar with one or more fatty acid esters in the presence of a transesterification catalyst.

Esters of a non-reducing sugar and fatty acids, in particular the monoesters and diesters derived from a sugar of this type are particularly valuable as surface-active agents and possess unique advantages because of their composition. For example, such surface-active agents are non-toxic, odourless and tasteless, they are not irritating to the skin and hydrolysis, for example, in the human and animal digestive tract to give normal food products. In contrast to most surface-active agents, the esters based on a sugar of this type and fatty acids are biodegradable both under aerobic and anaerobic conditions, and in contrast to most other non-ionogenic surface-active agents they are solid and can therefore easily be used in pulverulent or spray-dried products. The esters of a non-reducing sugar and fatty acids are good emulsifying agents and can therefore be used in detergents. In addition, the esters of a sugar of this type and fatty acids can be used as additives for foodstuffs, cosmetics, pharmaceutical preparations and agricultural products.

In spite of the abovementioned advantages, the esters of a non-reducing sugar with fatty acids have never been used on a large scale because of the disadvantages associated with the preparation thereof. There follows below a short discussion of the methods which have been proposed for the preparation of sugar esters of this type and which, because of technical or economic disadvantages, cannot be used easily on a large industrial large scale to obtain a product with a competitive cost price in relation to the other known surface-active agents.

The most "classical" method for the preparation of esters of a non-reducing sugar and fatty acids comprises the transesterification, reported, for example, in J. Amer. Oil Chem. Soc. vol. 34, 1957, pages 185–188, of sucrose with the methyl ester of a fatty acid in a solvent such as dimethylformamide and dimethylsulphoxide, in which both the sugar and the methyl ester of the fatty acid dissolve. This transesterification reaction is carried out in the presence of potassium carbonate as a catalyst and at a temperature of 90° C. and under considerably reduced pressure. It has emerged, however, that the solvents used, because of the toxicity thereof, have to be removed as completely as possible, which in practice entails considerable problems.

To solve the problems associated with the use of the abovementioned solvents for both the sugar and the esters of fatty acids, a method is proposed in J. Amer. Oil Chem. Soc. vol. 44, pages 307–309 (1967) for the preparation of a microemulsion system of sucrose and the ester of a fatty acid in propylene glycol. In this case the sugar, in the presence of an emulsifying agent, usually a salt of a fatty acid, and the methyl ester of a fatty acid are dissolved in propylene glycol, after which the solvent is removed under considerably reduced pressure. In this method it has, however, emerged that the problem is to obtain the reagents in a good microemulsion with the desired particle size, while, in addition, the removal of propylene glycol proceeds laboriously. Propylene glycol esters are also obtained as a by-product in this method.

A later modification of the solvent transesterification process in which water is used as the solvent is described in British Pat. No. 1,332,190. In this method the sugar is completely dissolved in the water in the presence of a fatty acid soap, a fatty acid ester and a transesterification catalyst, after which the mixture is dehydrated under reduced pressure and at elevated temperature so that a homogeneous melt is obtained. This process also presents problems as regards the heating of the product containing water under reduced pressure, the pressure having to be carefully regulated as a function of the temperature to prevent hydrolysis of the fatty acid ester. For this reason this method is undesirably complicated for use on an industrial scale.

In addition, a solvent-free transesterification method is described in J. Amer. Oil. Chem. Soc. 1970, vol. 47, pages 56–60. In this method sucrose is used in the molten state with the result that the method is carried out at a temperature of 170°–190° C. After a short time, however, the sugar begins to degrade to a black tar-like mass with the result that the reaction with the fatty acid ester has of necessity to take place very rapidly. Normally the reaction is finished within 20 min. and sometimes even after only 2 min. The reaction should be carried out in the presence of an anhydrous soap free of alkali metal which serves to solubilise the fatty acid ester in the molten sugar and to catalyse the transesterification. Alkoxides, alkali and common soaps are completely unsuitable as a catalyst in view of the fact that their presence results in a very rapid decomposition of the sugar and brings about a black colouration of the mixture. In view of the problems relating to controlling the reaction since the reaction has to be completed very quickly in order to prevent degradation of the sugar, this reaction can only be carried out on a laboratory scale and offers little promise for application Dn an industrial scale.

In addition, from British Pat. No. 1,399,053 a method is known for the preparation of a surface-active agent by the reaction of solid granular sucrose with at least a triglyceride in the presence of a basic transesterification catalyst at a temperature of 110°–140° C. under atmospheric pressure and in the absence of any solvent. As little water as possible should be present in the starting materials in view of the fact that approximately 1% by weight of water considerably retards the course of the reaction through the formation of lumps of sugar and in addition brings about an acceleration of the formation of soap. According to a preferred embodiment, in the method described in British Pat. No. 1,399,053 both the initiation period and the reaction period are considerably shortened by adding an emulsifying agent to the reaction mixture, advantageously in a quantity of 5–10% by weight. Besides di- and monoglycerides, the crude end product of this method, which contains surface-active substance, is suitable. It has emerged, however, that the reaction proceeds very sluggishly and takes about 8 hours or more.

Finally, in British Patent Application No. 2,065,634 a method is described for the preparation of surface-active substances containing sugar esters in which solid granular sucrose, at least a triglyceride of a fatty acid containing at least 8 carbon atoms and a basic transesterification catalyst are reacted at a temperature of 110°–140° C. under atmospheric pressure. However, the starting mixture should contain at least 10% by weight of fatty acid soap, while the optimum soap concentration in the starting material is 25–30% by weight. In addition, this soap should consist of potassium soap to an extent of at least 50%. This method therefore has disadvantages, for example because the end product is contaminated to a considerable extent with soap, in particular potassium soap.

Summarizing it can be stated that the solutions presented in the prior art discussed above as regards the problems of obtaining a non-reducing sugar and fatty acid esters in a form such that the reaction can be carried out in an efficient manner are not effective.

A method has therefore been sought in which a non-reducing sugar and fatty acid esters can be reacted with each other in a short time to obtain a product with a high yield and as few contaminants as possible.

It has been found that the object described above can be achieved if the reaction components are first fed through a worm shaft reactor known per se and operating at elevated temperature and pressure and the mass obtained from the said worm shaft reactor is then further reacted under reduced pressure and at elevated temperature.

By the method according to the invention a mixture of the reagents is, on the one hand, continuously fed through a worm shaft reactor or extruder device at elevated temperature and pressure, after which, on the other hand, the material emerging from the extruder device, after collection in a reactor vesel, reacts spontaneously and rapidly as a melt at elevated temperature and under reduced pressure.

The advantages of the method according to the invention over the methods known from the prior art are: capable of being carried out "simply" in a technological respect;
a semicontinuous method;
a short reaction time and
the reduced occurrence of decomposition reactions.

FIG. 1 shows a diagrammatic longitudinal section of a worm shaft reactor or extruder device which can be used in the method according to the invention. The housing of the worm shaft reactor is precisely matched to the outside circumference of the worm shaft and preferably possesses several, separate heating jackets ($V_1$ to $V_5$ incl.) capable of individual operation and cooling jackets ($K_1$ and $K_2$). In addition the worm shaft preferably possesses a cooling device ($K_3$). Over the entire length of the housing drilled holes are provided which are fitted with thermocouples $T_1$ to $T_6$ incl. In addition the worm shaft may be provided on the product removal side with a mixing head having a shell-shaped profile. A shell-shaped profile of this type is, however, not necessary since any type of mixing head can be used in the method according to the invention.

In the worm shaft reactors or extruder devices to be used in the method according to the invention, which provide transport under pressure, a thorough mixing of the reagents takes place, in which process a good temperature control and a good heat transfer can be achieved in a simple manner. Surprisingly, a mixing takes place in the worm shaft reactor which is such that the reaction in the mass, after the latter has been transferred to a reaction vessel, proceeds fairly rapidly at elevated temperature and under reduced pressure.

Figure 2:
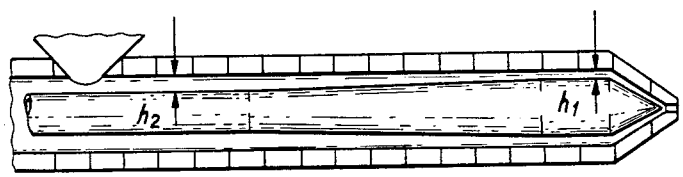

Although the embodiment of the worm shaft reactor to be used in the method according to the invention may vary within wide limits, worm shaft reactors are preferably used which have a compression ratio of 1.5–3 and also a length/diameter ratio of the worm of 10–20. For the calculation of the compression ratio reference is made to FIG. 2 (compression ratio = $h_1/h_2$).

The temperature prevailing in the worm shaft reactor is preferably such that the mass obtained from it is virtually completele melted. The said temperature is advantageously 170°–180° C.

In addition, worm shaft reactors with two worm shafts which rotate in opposite direction and therefore provide an extra large mixing action can be used.

The method according to the invention is preferably carried out using a methyl ester of a fatty acid as one of the starting materials. In this manner esters of sugar and fatty acid can be obtained in a very pure form. Another advantage is that the alcohol formed in the reaction, namely methanol, is the most advantageous alcohol as regards removability from the reaction mixture. In particular, as a result of removing the alcohol the equilibrium reaction proceeds to the sugar ester side. However, in addition to the methyl esters, ethyl esters and the like of fatty acids can also be used.

The fatty acid esters preferably used in the method according to the invention normally contain 8–22 carbon atoms in the fatty acid section. The fatty acids may or may not be branched and saturated or unsaturated. In addition, mixed fatty acid esters or fats can be used.

As the non-reducing sugar any commercially available solid sugar such as sucrose and sorbitol of any quality and grain size may be used. Preferably, however, coarse grains are reduced to grains with a size of 1 mm or less.

The invention is explained in more detail by reference to the exemplary embodiment below and to the comparative examples respectively, and the results obtained are shown in the graph in FIG. 4; the invention should not, however, be limited to the parameters reported in this exemplary embodiment.

EXAMPLE

A single-screw extruder was used for the extrusion of a mixture of 10% by weight of sodium stearate, 2.5% by weight of potassium carbonate, 25% by weight of methyl palmitate and 62.5% by weight of crystallized sugar (sucrose with a mean particle size of 0.75 mm). This single-screw extruder (see FIG. 1) was provided with 5 heating jackets ($V_1$ to $V_5$ incl. with a capacity of respectively 5, 5, 0.2, 1.4 and 2.1 kW), two cooling coils ($K_1$ and $K_2$) near the inlet opening of the extruder, a screw cooling device ($K_3$), and also a screw with a mixing head having a shell-shaped profile (LD = 16). Further characteristics of the extruder were:
total screw length: 0.86 m
length of mixing head with shell-shaped profile: 0.25 m
pitch of the screw: 45 mm
compression ratio: 2.

The temperature profile shown in FIG. 3 was obtained at an input of 13.2 kg/hour by adjusting the heating jackets $V_4$ and $V_5$ to 230° C., the jacket $V_3$ to maximum (0.2 kW) and the jacket $V_2$ to 10% of the maximum capacity (5 KW). The screw was cooled over the entire length with a quantity of 65 liters of water/hour and the housing of the extruder was cooled with the cooling coils $K_1$ and $K_2$, each using a quantity of 190 liters of water/hour.

With this setting of the extruder an extrusion product was obtained in which crystals were virtually no longer present and which had a temperature of 172°–177° C. A reaction vessel which was coupled to the extruder and which was provided with a double wall and a stirring device, and also had a capacity of at most 20 liters, was filled with a total of 4.4 kg of extrusion product in the course of 20 min. In the extruder the reaction had taken place only to a limited extent (less than 10%). After the said reaction vessel had been partially filled in the manner described above, the extrusion was stopped. The reaction was then continued in the vessel decoupled from the extruder at a temperature of 150° C. (by means of steam in the double wall of the reaction vessel) and under a pressure of 100 mbar. After the application of the reduced pressure the reaction rate increased enormously and it was possible to suppress the foam formation occurring under these circumstances by vigorous stirring. After only 90 minutes foam formation was no longer detectable and 94% of the methyl palmitate had been reacted (see FIG. 4).

COMPARATIVE EXAMPLE 1

Under the same conditions as in the above-described reaction vessel, namely at a temperature of 150° C. and under a pressure of 100 mbar, a reaction was carried out using 5 kg of a mixture which consisted of 10% by weight of sodium stearate, 2.5% by weight of potassium carbonate, 25% by weight of methyl palmitate and 62.5% by eight of castor sugar (sucrose with a mean particle size of 0.035 mm); no preliminary extrusion process was therefore carried out. After a heating-up time of 80 min., during which a reduced pressure of 100 mbar was applied after 40 min. to prevent condensation forming, the reaction temperature of 150° C. was reached. After approx. 20 min. at 150° C. foam formation occurred, which is characteristic of this type of reaction. The said foam formation stopped after 150 min. After a reaction time of 260 min. 94% of the methyl palmitate originally present had been converted (see FIG. 4).

COMPARATIVE EXAMPLE 2

A reaction was carried out under the conditions used in Comparative Example 1 using the same mixture as in the Comparative Example 1 but with the difference that instead of castor sugar crystallized sugar (sucrose with a mean particle size of 0.75 mm) was used. This mixture was heated to 150° C. in 100 min., in which process a reduced pressure of 100 mbar was applied after 45 min. to prevent condensation forming. After 60 min. at 150° C. foam formation occurred which, after a reaction time of 270 min., had virtually completely disappeared. After the said reaction time of 270 min. 80% of the quantity of methyl palmitate originally present has been converted (see FIG. 4).

We claim:

1. Process for the preparation of esters of a non-reducing sugar and one or more fatty acids by transesterification of a non-reducing sugar with one or more fatty acid esters in the presence of a transesterification catalyst, characterised in that the reaction components are first fed through a worm shaft reactor and operating at an elevated temperature at which the mass is substantially completely melted and elevated pressure corresponding to the compression ratio of the worm shaft reactor and the mass obtained from the said worm shaft reactor is then further reacted under reduced pressure sufficient to cause rapid reaction and at elevated temperature below the decomposition temperature of the reagents.

2. Process according to claim 1, characterised in that the temperature in the worm shaft reactor is such that the mass obtained from it is virtually completely melted.

3. Process according to claim 1, characterised in that the temperature of the mass obtained from the worm shaft reactor is 170°–180° C.

4. Process according to claim 1, characterised in that sucrose or sorbitol is used as a non-reducing sugar.

5. Process according to claim 1, characterised in that fatty acid esters are used which contain a fatty acid radical of 8–22 carbon atoms.

6. Process according to claim 1, characterised in that fats are used as fatty acid esters.

7. Process according to claim 1, characterised in that a methyl ester of a fatty acid is used as the fatty acid ester.

8. Process according to claim 1, characterised in that a worm shaft reactor is used in which the extremity of the worm situated at the output end of the worm shaft reactor is provided with a shell-shaped profile.

9. Process according to claim 1, characterised in that a worm shaft reactor is used which has a compression ratio of 1.5–3.

10. Process according to claim 1, characterised in that a worm shaft reactor is used, the length/diameter ratio of which has a value of 10–20.

* * * * *

UNITED STATES PATENT AND TRADEMARK OFFICE
CERTIFICATE OF CORRECTION

PATENT NO. : 4,778,881

DATED : October 18, 1988

INVENTOR(S) : Hermanus J. W. Nieuwenhuis and Gerardus M. Vianen

It is certified that error appears in the above-identified patent and that said Letters Patent is hereby corrected as shown below:

Column 2 Line 39 "Dn" should read --on--.

Column 3 Line 30 "vesel" should read --vessel--.

Column 4 Line 7 "completele" should read --completely--.

Column 4 Line 51 "(LD=16)" should read --(L/D=16)--.

Signed and Sealed this

Twentieth Day of June, 1989

*Attest:*

DONALD J. QUIGG

*Attesting Officer*  *Commissioner of Patents and Trademarks*